United States Patent [19]

Metz et al.

[11] B 3,985,790

[45] Oct. 12, 1976

[54] PHENOXYALKANE CARBOXYLIC ACID DERIVATIVE

[75] Inventors: Gunter Metz, Blaubeuren; Manfred Specker, Ehingen, Danube, both of Germany

[73] Assignee: Ludwig Merckle KG, Blaubeuren, Germany

[22] Filed: July 23, 1974

[21] Appl. No.: 491,052

[44] Published under the second Trial Voluntary Protest Program on March 2, 1976 as document No. B 491,052.

[52] U.S. Cl. .................................. 260/472; 424/310
[51] Int. Cl.² ........................................ C07C 103/78

[58] Field of Search ................................ 260/472

[56] References Cited
UNITED STATES PATENTS 3,475,470  10/1969  Rebstock ............................ 260/472

*Primary Examiner*—James A. Patten
*Attorney, Agent, or Firm*—Haseltine, Lake & Waters

[57] ABSTRACT

A novel pharmaceutically useful compound, the p-chlorophenoxyisobutyrate salt of 4-(p-chlorophenoxyacetyl-amino)-benzene carboxylic acid diethylaminoethyl ester, is disclosed, which has superior antilipemic and anticholesteremic properties.

1 Claim, No Drawings

PHENOXYALKANE CARBOXYLIC ACID DERIVATIVE

This invention relates to a new phenoxyalkane carboxylic acid derivative, namely, the salt of 4-(p-chlorophenoxyacetylamino)-benzencarboxylic acid diethylaminoethyl ester with p-chlorophenoxyisobutyric acid. The new substance has the following structural formula.

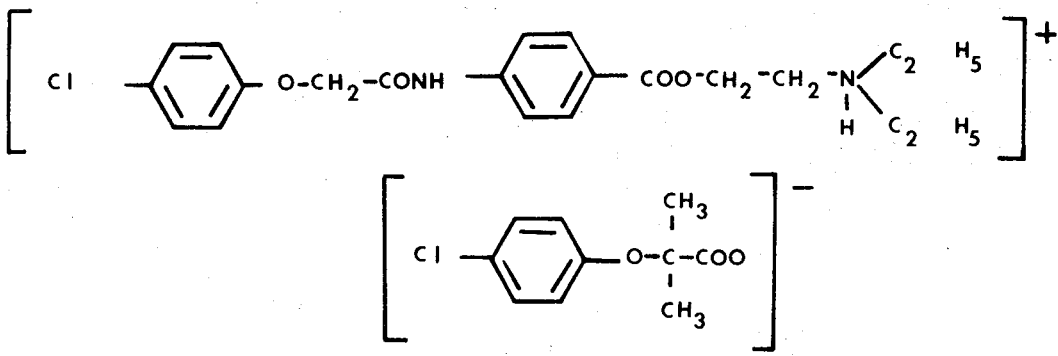

The invention also relates to a process for preparing the new phenoxyalkanecarboxylic acid derivative, in which p-chlorophenoxyacetic acid or a functionally equivalent derivative of this acid is reacted with 4-aminobenzoic acid diethylaminoethyl ester or a functionally equivalent derivative thereof and the basic reaction product so obtained is further reacted with p-chlorophenoxyisobutyric acid to form the corresponding salt.

Preferably, the amidation is carried out in the presence of a suitable catalyst such as phosphorus oxychloride, phosphorus trichloride, phosphorus pentachloride, dicyclohexylcarbodiimide or a similar imide.

Suitable derivatives of p-chlorophenoxyacetic acid are, for example, the acid chloride, the anhydride, or an ester.

The direct reaction of p-chlorophenoxyacetic acid with the amino compound or its functionally equivalent derivative is preferably carried out in an aromatic hydrocarbon solvent at a temperature between 100° and 150°C. Likewise, the reaction can be carried out in other suitable inert solvents or in the absence of a solvent. The solvent is in all cases preferably anhydrous. The mole ratio between the p-chlorophenoxyacetic acid and the amino compound in the reaction mixture is preferably between 1:1 and 2:1. The time for completion of the reaction amounts to about 2–10 hours. After separation of the residual acid and solvent, the amide product can be recovered in pure form by suitable crystallization.

The 4-(p-chlorophenoxyacetylamino)-benzoic acid diethylaminoethyl ester is then dissolved in suitable fashion in acetone or isopropanol and reacted with an equimolar quantity of p-chlorophenoxyisobutyric acid, likewise dissolved in acetone or isopropanol, respectively. The reaction is preferably carried out by heating the combined solutions to reflux temperature, after which the salt of the invention is precipitated by cooling.

The compound of the invention has a marked depressive effect on blood serum cholesterol and lipid levels and is well tolerated.

From French Pat. No. 1,552,793 it is known that certain phenoxyacetic acid derivatives including also 4-(p-chlorophenoxyacetylamino)-benzoic acid diethylaminoethyl ester and its salts have an influence on human lipid metabolism. In spite of this, it is a surprising discovery that the novel p-chlorophenoxyisobutyric acid salt of this known compound is far more effective than the basic parent compound and other salts. Furthermore, in contrast to the parent compound, the novel salt of this invention has not only a cholesterol depressing effect but also depresses triglyceride levels.

The therapeutic effectiveness of the salt of this invention ("clofibrinate") was compared with that of the fundamental parent substance, namely the 4-(p-chlorophenoxyacetylamino)-benzoic acid diethylaminoethyl ester, as well as clofibrate, that is the ethyl ester of clofibrinic acid, using SPF-Wistar rats. In these tests the compound in a vehicle was supplied orally for a period of 14 days. Twenty-four hours after the last dose blood analyses were made for determining the serum cholesterol and serum triglyceride levels.

In a first series of experiments, the effectiveness was studied in rats having normal blood lipid levels which were made hyperlipemic by means of a special fatty diet 1. This cholesterol-rich fatty diet 1 corresponded to that of Berger et al., Proc. Soc. Ex. Biol. (1969) 132,293.

In a second series young male rats of 80–90 grams weight were fed a fat and cholesterol-rich diet (fatty diet 2). The results of both these series are set forth in Table 1. The statistical significance (p) of the results is also given.

As the results demonstrate, the salt of this invention is especially effective against elevated cholesterol levels as well as against elevated triglyceride levels. Even at a dosage of 100 milligrams per kilogram the effectiveness is several times greater than that of 250 milligrams per kilogram of clofibrate. Thus, when its significantly lower toxicity in comparison to clofibrate is also considered it has a substantially greater therapeutic index.

Clofibrate itself is only slightly effective under hyperlipemic conditions or even fails completely so that an especially elevated cholesterol level is no longer decreased.

In comparison to the known ethyl-2-(p-chlorophenoxy)-isobutyrate (clofibrate) the salt of the invention shows a significantly lower toxicity.

| Compound | Animal | $LD_{50}$ (mg/kg) |
|---|---|---|
| Salt of this invention | Mouse | 2508 |
| Clofibrate | Mouse | 1150 |

The pharmaceuticals of this invention contain the effective compound of the invention and optionally the customary pharmaceutical carriers and adjuvants such as, for example, lactose, starch, talc, magnesium stearate, etc. The preferred form of administration is orally, for

TABLE 1

Antilipemic Effect with Fatty Diet (hypercholesteremic) and Fatty Diet 2 (high cholesterol-high fat)

| Test Group | Dose mg/kg | Fatty Diet 1 | | | | Fatty diet 2 | | | |
|---|---|---|---|---|---|---|---|---|---|
| | | Final Value Cholest. mg% | Decrease % | Final Value Triglycerides | Decrease % | Final Value Cholest. mg % | Decrease | Final Value Triglycerides | Decrease % |
| Control | — | 358.6 | — | 86.4 | — | 123.1 | — | 135.7 | — |
| Parent Compound | 100 | 330.6 | 7.8 | 114.9 | — | | | | |
| | 250 | 269.4+++ | 24.9 | 101.6 | — | | | | |
| Clofibrirate | 100 | | | | | 102.6 | 16.3 | 88.0++ | 35.2 |
| Clofibrate | 250 | 347.9 | 3.0 | 75.6 | 12.5 | 133.3 | — | 107.7+ | 20.6 |
| | 1000[1] | 245.4+++ | 31.6 | 120.3 | — | | | | |

+p<0.05
++p<0.01
+++p<0.001
[1] 3 of 10 animals died example, in the form of capsules or tablets. The compound of the invention is administered as required in oral or rectal daily dosages of 100 to 1,000 milligrams, preferably 100 to 500 milligrams, in the usual pharmaceutical forms.

The following examples are intended to illustrate the invention without restricting its scope.

EXAMPLE 1

84.9 grams (0.455 moles) of p-chlorophenoxyacetic acid and 20.8 grams (0.152 moles) of phosphorus trichloride were suspended with stirring in 200 millimeters of toluene. 71.6 grams (0.303 moles) of 4-aminobenzoic acid diethylaminoethyl ester were added, and the mixture was heated for four hours under reflux. The evolved hydrochloric acid was driven off through the condenser. The reaction charge was diluted with 500 millimeters of chloroform, washed with dilute sodium hydroxide and water, and evaporated in a rotary evaporator. The residue was crystallized from ethanol, and 88.7 grams (72.2% of the theoretical amount) of 4-(p-chlorophenoxyacetylamino)-benzoic acid diethylaminoethylester were recovered as colorless crystals having a melting point of 132°–133°C.

| Elemental analysis: | | C | H | N | Cl |
|---|---|---|---|---|---|
| $C_{21}H_{25}ClN_2O_4$ | Calculated | 62.29 | 6.22 | 6.92 | 8.75 |
| (404.9) | Found | 62.11 | 6.19 | 7.10 | 8.61 |
| IR (KBr): | 3490/cm (—NH); 1705/cm (ester carbonyl), 1674/cm (Amide carbonyl) | | | | |

The ester so obtained was dissolved in acetone and this solution was mixed with a solution of p-chlorophenoxyisobutyric acid also in acetone and heated to reflux temperature. When the mixture was cooled the p-chlorophenoxyisobutyrate (M.P. 124°–125°C) separated. p-chlorophenoxyisobutyrate: MP 124–125

| Elemental analysis: | | C | H | N | Cl |
|---|---|---|---|---|---|
| $C_{31}H_{36}Cl_2N_2O_7$ | Calculated | 60.10 | 5.85 | 4.52 | 11.44 |
| (619.55) | Found | 60.07 | 5.98 | 4.52 | 11.28 |

EXAMPLE 2

Tablets

| Compound of Example 1 | 150 mg |
|---|---|
| Microfine cellulose | 80 mg |
| Lactose | 80 mg |
| Potato starch | 90 mg |
| Talc | 14 mg |
| Magnesium stearate | 6 mg |

EXAMPLE 3

Capsules

| Compound of Example 1 | 200 mg |
|---|---|
| Cornstarch | 15 mg |
| Lactose | 30 mg |

EXAMPLE 4

Liquid

| Compound of Example 1 | 20 g |
|---|---|
| Propylene glycol | 20 ml |
| Ethanol | 25 ml |
| Perfume | 0.1 g |
| Water | q.s.p. 100 ml |

EXAMPLE 5

Ampoule solution

| Compound of Example 1 | 50 mg |
|---|---|
| Water (with solution adjuvant) | q.s.p. 1.0 ml |

EXAMPLE 6

Suppositories

| Compound of Example 1 | 150 mg |
|---|---|
| Semi-synthetic partial glyceride containing about 5% glyceryl monostearate | 1950 mg |

We claim:
1. 4-(p-chlorophenoxyacetylamino)-benzoic acid diethylaminoethyl ester p-chlorophenoxyisobutyrate.

* * * * *